United States Patent [19]

Pohlke et al.

[11] 4,122,180
[45] Oct. 24, 1978

[54] ISOQUINOLINES AND ANTI-DEPRESSANTS CONTAINING THEM

[75] Inventors: Rolf Pohlke; Wighard Strehlow; Helmut Mueller-Calgan; Christoph Seyfried, all of Darmstadt, Fed. Rep. of Germany

[73] Assignee: Merck Patent Gesellschaft mit Beschraenkter Haftung, Fed. Rep. of Germany

[21] Appl. No.: 806,240

[22] Filed: Jun. 13, 1977

[30] Foreign Application Priority Data

Jun. 14, 1976 [DE] Fed. Rep. of Germany ....... 2626629

[51] Int. Cl.$^2$ .................... A61K 31/47; C07D 401/04
[52] U.S. Cl. ............................. 424/258; 260/287 CE; 260/288 CE
[58] Field of Search ................. 260/288 CE, 287 CE; 424/258

[56] References Cited

U.S. PATENT DOCUMENTS

| | | | |
|---|---|---|---|
| 3,479,358 | 11/1969 | Hansen et al. | 260/286 |
| 3,901,897 | 8/1975 | Hauck | 260/288 R |
| 4,048,177 | 9/1977 | Black | 260/288 R |

OTHER PUBLICATIONS

Berger et al., Chemical Abstracts, vol. 42, 3403*i*-3404*f* (1947).
Sugimoto et al., Chemical Abstracts, vol. 51, 16, 563*i* (1957).
Barrett et al., Chemical Abstracts, vol. 52, 11,845*e* (1958).
Nakananishi et al., Chemical Abstracts, vol. 79, 115,448*a* (1973).

*Primary Examiner*—Paul M. Coughlan, Jr.
*Assistant Examiner*—Diana G. Rivers
*Attorney, Agent, or Firm*—Millen & White

[57] ABSTRACT

Isoquinolines of the formula

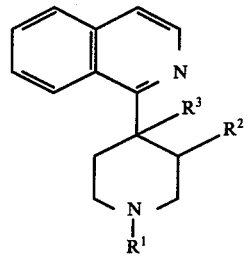

wherein $R^1$ is H or alkyl of 1 - 4 carbon atoms, $R^2$ is H and $R^3$ is OH or $R^2$ and $R^3$ collectively are a C—C bond, and physiologically acceptable acid addition salts thereof have anti-depressant activity and can be prepared by solvolyzing or hydrogenolyzing a compound of the formula

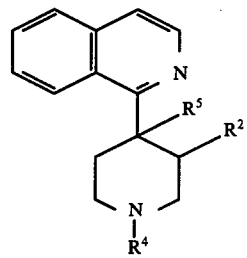

or an acid addition salt thereof, wherein $R^4$ is $R^1$ or $R^6$, $R^5$ is $OR^7$ or, when $R^4$ is $R^6$, $R^3$; $R^6$ and $R^7$ are radicals which can be split off solvolytically or hydrogenolytically and $R^1$ and $R^2$ are as above; and the optional step of dehydrating a resulting carbinol ($R^2$ is H, $R^3$ is OH) and/or treating a resulting compound ($R^1$ is H) with a N-alkylating agent and/or converting a resulting base to a physiologically acceptable acid addition salt by treatment with and acid.

12 Claims, No Drawings

ISOQUINOLINES AND ANTI-DEPRESSANTS CONTAINING THEM

BACKGROUND OF THE INVENTION

This invention relates to novel isoquinoline compounds, which have antidepressant activity.

SUMMARY OF THE INVENTION

In a compositional aspect, this invention relates to novel compounds of Formula I,

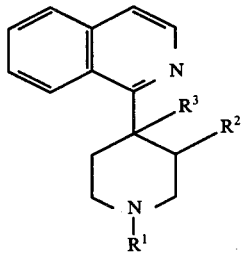

I wherein $R^1$ is H or alkyl of 1-4 carbon atoms; $R^2$ is H and $R^3$ is OH or $R^2$ and $R^3$ collectively are a C—C bond, or a physiologically acceptable acid addition salt thereof.

In another compositional aspect, this invention relates to a pharmaceutical composition, comprising an amount per unit dosage effective to evoke a CNS antidepressant effect of a compound of Formula I, in admixture with a pharmaceutically acceptable carrier.

In a method of use aspect, this invention relates to a method of treating a patient in a state of depression, comprising administering to the affected patient an antidepressant amount of a compound of Formula I.

In a preparative aspect, this invention relates to a process for preparing a compound of Formula I, wherein $R^2$ is H and $R^3$ is OH, comprising the step of solvolyzing or hydrogenolyzing a compound of the Formula II

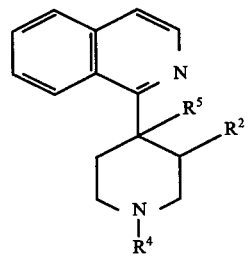

II or an acid addition salt thereof, wherein $R^4$ is H, alkyl of 1-4 carbon atoms or $R^6$; $R^2$ is H; $R^5$ is $OR^7$ or, when $R^4$ is $R^6$, is OH; $R^6$ and $R^7$ are alkanoyl or aroyl of up to 10 carbon atoms or benzyl or $R^7$ is Li or MgHal and Hal is Cl, Br, or I, provided that at least one of $R^4$ or $R^5$ is $R^6$ or $OR^7$ respectively.

This invention further relates to novel compounds of Formula II.

DETAILED DESCRIPTION

Compounds of Formula I include carbinols (I, $R^2$ is H, $R^3$ is OH) and the corresponding dehydration products (I, $R^2$ and $R^3$ collectively are a C—C bond). $R^1$ is preferably methyl, hydrogen or ethyl. $R^1$ can also be propyl, isopropyl, butyl, isobutyl, sec.-butyl or tert.-butyl.

Preferred compounds of Formula I(a) and I(b) which follow, correspond to compounds of Formula I, wherein, in I(a) $R^1$ is H, methyl or ethyl, $R^2$ is H and $R^3$ is OH, and in I(b) $R^1$ is H, methyl or ethyl and $R^2$ and $R^3$ collectively are a C—C bond, and physiologically acceptable acid addition salts thereof.

Starting materials of Formula II correspond to those of Formula I, except that one or both of radicals $R^1$ and $R^3$ is present in a functionally-modified form which can be cleaved by solvolysis or hydrogenolysis. The nature of $R^6$ and $R^7$ is not critical since they are split off in the process of the invention. Exemplary radicals which can be removed solvolytically are, acyl, preferably alkanoyl or aroyl of up to 10 atoms, most preferably acetyl and benzoyl. $R^7$ can also be a metal, preferably Li or MgHal, wherein Hal is Cl, Br or I.

Radicals which can be removed by hydrogenolysis include, but are not limited to, benzyl and substituted benzyl e.g., p-methoxybenzyl and diphenylmethyl.

Compounds of Formula I are in other respects prepared by known methods, described in standard works such as Houben-Weyl, Methoden der organischen Chemie (Methods of Organic Chemistry), Georg-Thieme-Varlag, Stuttgart, under reaction conditions known and suitable for the reactions mentioned. Variants which are known but not described here in more detail can also be used.

Starting materials of Formula II are also new, but can be prepared by known processes. The starting materials can also be formed in situ in such a way that they are not isolated from the reaction mixture but immediately further reacted to give the compounds of Formula I, which procedure is generally particularly preferred.

Starting materials of Formula II ($R^2$ is H, $R^5$ is O-acyl, preferably O-benzoyl) can be obtained, for example, by reacting a 1-cyano-2-acyl-1,2-dihydroisoquinoline that is a "Reissert compound" of isoquinoline, preferably 1-cyano-2-benzoyl-1,2-dihydroisoquinoline, with a 1-$R^4$-piperidin-4-one.

The reaction is preferably carried out in the presence of a base, for example, in aqueous sodium hydroxide solution, or with sodium hydroxide in an inert solvent, such as dimethylformamide.

Starting materials of Formula II ($R^2$ is H, $R^5$ is OLi) are obtainable, for example, by reacting 1-isoquinolyl-lithium with a 1-$R^4$-piperidin-4-one under customary conditions for this type of organometallic reaction, for example, in an ether, such as diethyl ether. Starting materials of Formula II $R^5$ is $R^6$, $R^2$ and $R^5$ together are a C—C bond, are obtainable from compounds of Formula II ($R^4$ is $R^6$, $R^2$ is H, $R^5$ is O-acyl) by successive solvolysis and dehydration, preferably under conditions described below.

Solvolysis of a compound of Formula II ($R^6$ and/or $R^7$ is a radical which can be removed solvolytically) is preferably by hydrolysis, and can be carried out in an acid, neutral or alkaline medium. The conditions selected depend on the nature of $R^6$ and/or $R^7$ being split off. If one of these, particularly $R^7$, is acyl, especially acetyl or benzoyl, the hydrolysis is preferably carried out with strong acid, preferably a mineral acid, such as hydrochloric acid, sulfuric acid or phosphoric acid; or a strong base, preferably an alkali metal hydroxide or alkaline earth metal hydroxide, such as sodium, potassium or calcium hydroxide, in an aqueous, aqueous-alcoholic or alcoholic medium. In addition to water, preferred solvents are alcohols, such as methanol, ethanol, isopropanol or butanol. Other inert organic solvents can also be present, for example an ether, such as dioxane. The solvolysis can preferably be effected at temperatures between 0° and 150°. Temperatures between 60° to 140°, particularly between 78° and 120°, are preferred.

Metal alcoholates of Formula II ($R^2$ is H, $R^5$ is OLi or OMgHal) can be split under milder conditions, for example with water, aqueous ammonium chloride solution or dilute mineral acid, such as hydrochloric acid, at temperatures between 0° and 30°.

Hydrogenolysis of compounds of Formula II wherein $R^6$ and/or $R^7$ are radicals which can be split off hydrogenolytically is preferably effected with hydrogen in the presence of a catalyst, for example, a noble metal catalyst, such as palladium or platinum, or another heavy metal catalyst, such as Raney nickel, at temperatures between 0° and 150°, preferably at room temperature, in an inert solvent. Exemplary solvents are alcohols, such as methanol or ethanol; ethers, such as tetrahydrofuran or dioxane; esters, such as ethyl acetate or carboxylic acids, such as acetic acid. The reaction is preferably done under pressures between 1 and 200 atmospheres.

If desired, a resulting carbinol of Formula I ($R^2$ is H, $R^3$ is OH) can be treated with a dehydrating agent to form a corresponding unsaturated compound of Formula I ($R^2$ and $R^3$ collectively are a C—C bond). Typical dehydrating agents are strong acids, preferably sulfuric acid or phosphoric acid or, most preferably, polyphosphoric acid. Reaction temperatures are preferably between 100° and 160°. An inert solvent can, but need not necessarily, be added during the dehydration.

If the reaction is carried out under drastic conditions, solvolysis and dehydration can be carried out in a one-pot process without isolating the carbinol of Formula I ($R^2$ is H, $R^3$ is OH). For example, by heating an acyl compound of Formula II ($R^2$ is H, $R^5$ is O-acyl, preferably $OCOC_6H_5$) with polyphosphoric acid to about 160°, the corresponding unsaturated compound of Formula I ($R^2$ and $R^3$ collectively are a C—C bond) can be obtained directly.

If desired, a resulting compound of Formula I ($R^1$ is H) can be alkylated on the piperidine nitrogen to produce compounds of Formula I ($R^1$ is alkyl of 1-4 carbon atoms). Exemplary suitable N-alkylating agents are corresponding alkyl halides, for example, methyl chloride, methyl bromide, methyl iodide, ethyl chloride, ethyl bromide, ethyl iodide, n-propyl chloride, bromide and iodide; corresponding sulfates, such as dimethyl sulfate; corresponding sulfonic acid esters, such as p-toluenesulfonic acid methyl ester. A methyl group can also be introduced, for example by treatment with formic acid and aqueous formaldehyde solution, preferably by heating to temperatures between 50° and 100° for several hours. N-Alkylation is preferably carried out in the presence or absence of an inert solvent at temperatures between about 0° and about 120°, preferably between 40° and 100°. A catalyst can be used, preferably a base, such as potassium tert.-butylate.

Alkylation can also be effected by treatment of the secondary base of Formula I ($R^1$ is H) with an aldehyde or ketone in the presence of hydrogen and a hydrogenation catalyst, for example, Raney nickel, at temperatures between about 50° and 100° and under pressures of between about 1 and 200 atmospheres. The corresponding isopropyl compound of Formula I ($R^1$ is isopropyl) is thus obtained with acetone.

The alkylation can also be done in several steps. For example, a compound of Formula I ($R^1$ is H) can be acylated initially in a known manner, as by acetylation with acetic anhydride/pyridine, and the resulting N-acylated product, for example, an N-acetyl product, subsequently reduced to the desired tertiary amine, for example, using a complex metal hydride, such as $LiAlH_4$, in an inert solvent, such as diethyl ether or tetrahydrofuran, preferably at temperatures between 20° and 60°.

A resulting base of Formula I can be converted to the appropriate acid addition salt by reaction with an acid. Acids suitable for this reaction are those which give physiologically acceptable salts. Thus, inorganic acids, for example, sulfuric acid; hydrogen halide acids, such as hydrochloric acid or hydrobromic acid; phosphoric acids, such as orthophosphoric acid; nitric acid; and sulfamic acid, can be used. Organic acids can also be used, e.g., aliphatic, alicyclic, araliphatic, aromatic or heterocyclic monobasic or polybasic carboxylic or sulfonic acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicyclic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid and naphthalene-monosulfonic and naphthalene-disulfonic acids.

If desired, free bases of Formula I can be liberated from salts thereof by treatment with a strong base, such as sodium hydroxide or potassium hydroxide or sodium carbonate or potassium carbonate.

Compounds of Formula I and physiologically acceptable acid addition salts thereof possess valuable pharmacological properties. More particularly, they exhibit activity on the central nervous system, especially antidepressant activity. For example, they have:

(a) an anticataleptic effect which can be determined against tetrabenazine in rats by the methods of Giurgea et al., Medicina Experimentalis, Volume 9 (1963), pages 249–262, (b) an antiptotic effect which can be determined, for example, against reserpine by the method of Domenjoz and Theobald, Arch. int. pharmacodyn., Volume 120 (1959), page 450 et seq., with evaluation according to Rubin et al., J. Pharmacol. Exp. Therap., Volume 120 (1957), pages 125–136; and (c) an increase in and/or prolongation of the effects of excitation and temperature increase of the central nervous system caused by D-amphetamine sulfate, for example, 1.5 mq./kq. administered subcutaneously 1 hour after the test substance, which is likewise administered subcutaneously or by aggregation by putting 5 rats together in one glass, according to Mueller-Calgan et al. in Zippel, H.P. (Editor): Memory and Transfer of Information, Plenum Press, New York - London, 1973, pages 87–125.

Compounds of the Formula I affect the biogenic amines of the central nervous system. For example, they lead to:

(a) inhibition of absorption of noradrenaline, 5-hydroxytryptamine and dopamine in synaptosomes in vitro, as determined by the method of Kannengiesser et al., Biochem. Pharmacol., Volume 22 (1973), pages 73-84;

(b) in vivo inhibition of tyramine-induced release of catecholamine in the brain, demonstrated in accordance with Carlsson et al., Europ. J. Pharmacol., Volume 5 (1969), pages 357-366; 367-373; and (c) inhibition of phosphodiesterase from bovine hearts and of thrombocyte aggregation, detected, for example, in rabbits by the Born test in vitro and ex vivo in accordance with Thrombos. Diathes. haemorrh., Volume 26, (1971), pages 192-202.

Compounds of Formula I and physiologically acceptable acid addition salts thereof can thus be used as medicaments and also as intermediates for the preparation of other medicaments.

The term "antidepressant" as used herein is well known in the art and designates drugs for the treatment of depressions, as outlined in detail, f.e., in Louis S. Goodman and Alfred Gilman, The Pharmacological Basis of Therapeutics, 4th Edition, The Macmillan Co., London and Toronto, 1971, pages 181-195.

The new compounds of Formula I and their physiologically acceptable acid addition salts can be used for the preparation of pharmaceutical formulations by conversion into a suitable dosage form together with at least one excipient or auxiliary and optionally together with one or more further active compound(s). The formulations thus obtained can be employed as medicaments in human or veterinary medicine.

Excipients are organic or inorganic substances which are suitable for enteral, for example, oral, or parenteral administration for topical application and which do not react with the new compouds, for example, water, vegetable oils, benzyl alcohols, polyethylene glycols, gelatin, carbohydrates, such as lactose or starch, magnesium stearate, talc and white petroleum jelly.

Tablets, dragees, capsules, syrups, elixirs, drops or suppositories, in particular, are used for enteral administration; oily or aqueous solutions as well as suspensions, emulsions or implants, are preferably used for parenteral administration; and ointments, creams or powders are used for topical application.

The new compounds can also be lyophilized and the resulting lyophilizates used, for example, to prepare injectable formulations. The formulations indicated can be sterilized and/or contain auxiliaries, such as lubricants, preservatives, stabilizers and/or wetting agents, emulsifiers, salts for influencing the osmotic pressure, buffer substances, dyestuffs, flavoring and/or perfumes. If desired, they can also contain one or more other active compounds, for example one or more vitamins.

As a rule, the substances of the invention are administered analogously to known commercially available psychopharmacological agents, for example, imipramine, preferably in dosages between about 2 and 500 mg., most preferably between 10 and 50 mg. per dosage unit. The daily dosage is preferably between about 0.05 and 10 mg./kg. of body weight. However, the specific dose for each particular patient depends on the most diverse factors, for example, on the activity of the specific compound employed and on the age, body weight, general state of health, sex, on diet, time and method of administration rate of excretion, medicament combination and severity of the particular illness for which the therapy is applied. Oral administration is preferred.

Each of the compounds of Formula I mentioned in the examples which follow is particularly suitable for the preparation of pharmaceutical formulations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way.

In the examples which follow, "customary work up" means:

Water is added, if necessary. The mixture is extracted with an organic solvent, such as benzene, chloroform or dichloromethane, the organic phase is separated off, dried over sodium sulfate and filtered and the filtrate is evaporated and purified by chromatography and/or crystallization.

EXAMPLE 1

346 g. of 1-methyl-4-benzoyloxy-4-(1-isoquinolyl)-piperidine hydrochloride (m.p. 269°, from isopropanol), obtainable by adding 30 g. of NaH in portions to a solution of 260 g. of 1-cyano-2-benzoyl-1,2-dihydroiosquinoline and 120 g. of 1-methylpiperidin-4-one in 950 ml. of dimethylformamide, with stirring, and allowing the mixture to stand overnight, are heated under reflux with 1,400 ml. of 25% hydrochloric acid for 40 hours. The mixture is cooled and worked up in the customary manner to give 1-methyl-4-(1-isoquinolyl)-piperidin-4-ol, m.p. 265°-266°.

EXAMPLES 2 TO 9

In accordance with Example 1, 4-benzoyloxy-4-(1-isoquinolyl)-piperidine or 1-ethyl-, 1-n-propyl-, 1-isopropyl-, 1-n-butyl-, 1-isobutyl-, 1-sec.-butyl- or 1-tert.-butyl-4-benzoyloxy-4-(1-isoquinolyl)-piperidine give:

2. 4-(1-Isoquinolyl)-piperidin-4-ol, m.p. 138°-140°.
3. 1-Ethyl-4-(1-isoquinolyl)-piperidin-4-ol, dihydrochloride, m.p. 275°-276°.
4. 1-n-Propyl-4-(1-isoquinolyl)-piperidin-4-ol.
5. 1-Isopropyl-4-(1-isoquinolyl)-piperidin-4-ol, m.p. 118°-119°.
6. 1-n-Butyl-4-(1-isoquinolyl)-piperidin-4-ol.
7. 1-Isobutyl-4-(1-isoquinolyl)-piperidin-4-ol.
8. 1-sec.-Butyl-4-(1-isoquinolyl)-piperidin-4-ol.
9. 1-tert.-Butyl-4-(1-isoquinolyl)-piperidin-4-ol.

EXAMPLE 10

1-Methyl-4-benzoyloxy-4-(1-isoquinolyl)-piperidine (346 g.) are heated under reflux with 1,500 ml. of 10% ethanolic KOH solution for 24 hours. The mixture is evaporated and worked up in the customary manner to give 1-methyl-4-(1-isoquinolyl)-piperidin-4-ol, dihydrochloride, m.p. 265°-266°.

EXAMPLE 11

Analogously to Example 10, 1-acetyl-4-benzoyloxy-4-(1-isoquinolyl)-piperidine (m.p. 186°-189°), obtainable from 1-cyano-2-benzoyl-1,2-dihydroisoquinoline and 1-acetylpiperidin-4-one gives 4-(1-isoquinolyl)-piperidin-4-ol, m.p. 138°-140°.

EXAMPLE 12

A solution of 11.3 g. of 1-methylpiperidin-4-one in 120 ml. of ether is added dropwise to a stirred isoquinolyl-1-lithium solution, freshly prepared from 20.8 g. of 1-bromoisoquinoline and n-butyllithium in 400 ml. of ether, at 0°, under dry nitrogen. The mixture is stirred for 2 hours more at 0°. Water (50 ml.) and then 100 ml. of 5% hydrochloric acid are added dropwise to decompose the lithium 1-methyl-4-(1-isoquinolyl)-piperidin-4- olate formed. The mixture is worked up in the customary manner to give 1-methyl-4-(1-isoquinolyl)-piperidin-4-ol, dihydrochloride, m.p. 265°–266°.

EXAMPLE 13

1-Methyl-4-benzoyloxy-4-(1-isoquinolyl)-piperidine (34.6 g.) are heated to 160° with 150 g. of freshly prepared polyphosphoric acid for 24 hours. The mixture is cooled. Water is added and the mixture is worked up in the customary manner with sodium hydroxide solution and chloroform. The product is 1-(1-methyl-3,4-dehydro-4-piperidyl)-isoquinoline; dihydrochloride, m.p. 228°–230°. Maleate, m.p. 171°–173°.

EXAMPLE 14

1-Methyl-4-(1-isoquinolyl)-piperidin-4-ol (24.2 g.) is heated to 140° with 115 g. of freshly prepared polyphosphoric acid for 24 hours. The mixture is cooled. Water is added and the mixture is worked up with sodium hydroxide solution and chloroform. The resulting 1-(1-methyl-3,4-dehydro-4-piperidyl)-isoquinoline has a dihydrochloride melting at 228°–230°.

EXAMPLES 15 TO 22

In accordance with Example 14, the corresponding carbinols give:
15. 1-(3,4-Dehydro-4-piperidyl)-isoquinoline, dihydrochloride, m.p. 260°–270° (decomposition).
16. 1-(1-Ethyl-3,4-dehydro-4-piperidyl)-isoquinoline, dihydrochloride, m.p. 234°–238° (decomposition).
17. 1-(1-n-Propyl-3,4-dehydro-4-piperidyl)-isoquinoline.
18. 1-(1-Isopropyl-3,4-dehydro-4-piperidyl)-isoquinoline.
19. 1-(1-n-Butyl-3,4-dehydro-4-piperidyl)-isoquinoline.
20. 1-(1-Isobutyl-3,4-dehydro-4-piperidyl)-isoquinoline.
21. 1-(1-sec.-Butyl-3,4-dehydro-4-piperidyl)-isoquinoline.
22. 1-(1-tert.-Butyl-3,4-dehydro-4-piperidyl)-isoquinoline.

EXAMPLE 23

A solution of 318 g. of 1-benzyl-4-(1-isoquinolyl)-piperidin-4-ol, obtainable by reacting 1-cyano-2-benzoyl-1,2-dihydroisoquinoline with 1-benzylpiperidin-4-one to give 1-benzyl-4-benzoyloxy-4-(1-isoquinolyl)-piperidine, which is subsequently hydrolyzed in 5 l. of methanol, is hydrogenated on 60 g. of 5% Pd-on-charcoal at 20° under 1 atmosphere of hydrogen. The mixture is filtered and the filtrate is evaporated to give 4-(1-isoquinolyl)-piperidin-4-ol, m.p. 138°–140°.

EXAMPLE 24

A mixture of 228 g. of 4-(1-isoquinolyl)-piperidin 4-ol, 1,200 ml. of formic acid and 200 g. of a 40% formaldehyde solution is heated at 60° for 3 hours and then at 100° for 12 hours and subsequently evaporated. After customary the work up with sodium hydroxide solution and chloroform, 1-methyl-4-(1-isoquinolyl)-piperidin-4-ol, dihydrochloride, m.p. 265°–266°, is obtained.

EXAMPLE 25

A mixture of 2.28 g. of 4-(1-isoquinolyl)-piperidin-4-ol, 1 ml. of pyridine, 1 ml. of acetic anhydride and 20 ml. of benzene is stirred for 3 hours at 25°. The crude 1-acetyl-4-(1-isoquinolyl)-piperidin-4-ol obtained after the customary work up is heated under reflux with 0.7 g. of LiAlH$_4$ in 40 ml. of THF for 24 hours, under nitrogen. The mixture is worked up with sodium hydroxide solution and chloroform in the customary manner to give 1-ethyl-4-(1-isoquinolyl)-piperidin-4-ol, m.p. 275°–276°.

EXAMPLE 26

A mixture of 22.8 g. of 4-(1-isoquinolyl)-piperidin-4-ol, 20 g. of Raney nickel and 250 ml. of acetone is hydrogenated at 88° under 100–125 atmospheres for 12 hours, cooled and filtered. The filtrate is evaporated and the residue is chromatographed on silica gel. 1-Isopropyl-4-(1-isoquinolyl)-piperidin-4-ol, m.p. 118°–119°, is eluted with chloroform/methanol (9:1).

The examples which follow relate to pharmaceutical formulations which contain isoquinolines of Formula I or acid addition salts thereof:

EXAMPLE A: TABLETS

A mixture of 1 kg. of 4-(1-isoquinolyl)-piperidin-4-ol, 4 kg. of lactose, 1.2 kg. of potato starch, 0.2 kg. of talc and 0.1 kg. of magnesium stearate is pressed to give tablets in the customary manner in such a way that each tablet contains 10 mg. of active compound.

EXAMPLE B: DRAGEES

As in Example A, tablets are pressed which each contain 25 mg. of 1-methyl-4-(1-isoquinolyl)-piperidin-4-ol dihydrochloride. These are subsequently coated in the customary manner with a coating of sucrose, potato starch, talc, tragacanth and a dyestuff.

EXAMPLE C: CAPSULES 1-(1-Methyl-3,4-dehydro-4-piperidyl)-isoquinoline dihydrochloride (5 kg.) is charged in the customary manner into hard gelatin capsules so that each capsule contains 50 mg. of active compound.

Tablets, dragees and capsules which contain one or more of the other active compounds of Formula I and/or their physiologically acceptable acid addition salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of the formula

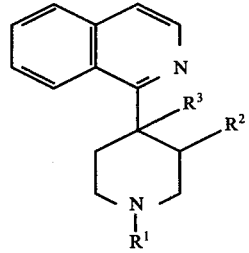

wherein $R^1$ is H or alkyl of 1–4 carbon atoms; $R^2$ is H and $R^3$ is OH or $R^2$ and $R^3$ collectively are a C—C bond; or a physiologically acceptable acid addition salt thereof.

2. A compound of claim 1, wherein $R^2$ is H and $R^3$ is OH.

3. A compound of claim 1, wherein $R^2$ and $R^3$ collectively are a C—C bond.

4. 4-(1-Isoquinolyl)-piperidin-4-ol, a compound of claim 1.

5. 1-Methyl-4-(1-isoquinolyl)-piperidin-4-ol, a compound of claim 1.

6. 1-Ethyl-4-(1-isoquinolyl)-piperidin-4-ol, a compound of claim 1.

7. 1-(3,4-Dehydro-4-piperidyl)-isoquinoline, a compound of claim 1.

8. 1-(1-Methyl-3,4-dehydro-4-piperidyl)-isoquinoline, a compound of claim 1.

9. 1-(1-Ethyl-3,4-dehydro-4-piperidyl)-isoquinoline, a compound of claim 1.

10. A pharmaceutical composition comprising an amount per unit dosage effective to evoke a CNS antidepressant effect of a compound of claim 1, in admixture with a pharmaceutically acceptable carrier.

11. A method of treating a patient in a state of depression, comprising administering to the affected patient an antidepressant amount of a compound of claim 1.

12. A compound of the formula

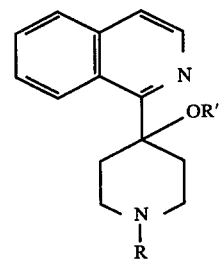

wherein R is H, alkyl of 1-4 carbon atoms or R''; R'' is alkanoyl or aroyl of up to 10 carbon atoms or benzyl; and R' is R'', Li or MgHal and Hal is Cl, Br or I.

* * * * *